United States Patent
Jiang et al.

(10) Patent No.: US 6,800,625 B2
(45) Date of Patent: Oct. 5, 2004

(54) SUBSTITUTED 2,4-DIHYDRO-PYRROLO[3,4-B]QUINOLIN-9-ONE DERIVATIVES USEFUL AS PHOSPHODIESTERASE INHIBITORS

(75) Inventors: Weiqin Jiang, Raritan, NJ (US); Zhihua Sui, Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/463,941

(22) Filed: Jun. 17, 2003

(65) Prior Publication Data

US 2004/0006079 A1 Jan. 8, 2004

Related U.S. Application Data

(60) Provisional application No. 60/389,904, filed on Jun. 19, 2002.

(51) Int. Cl.[7] .................. A61K 31/4365; A61K 31/437; C07D 471/02; C07D 471/18
(52) U.S. Cl. ............................. 514/232.8; 514/252.12; 514/292; 514/293; 544/126; 544/336; 546/62; 546/63; 546/81; 546/82
(58) Field of Search ................................ 544/126, 336; 546/62, 63, 81, 82; 514/232.8, 252.13, 292, 293

(56) References Cited

U.S. PATENT DOCUMENTS

| | | |
|---|---|---|
| 4,235,907 A | 11/1980 | Pfenninger |
| 5,126,352 A | 6/1992 | Ganguly et al. |
| 5,250,534 A | 10/1993 | Bell et al. |
| 5,346,901 A | 9/1994 | Bell et al. |
| 6,043,252 A | 3/2000 | Bombrun |
| 6,335,346 B1 | 1/2002 | Fourtillan et al. |
| 6,492,358 B2 | 12/2002 | Sui et al. |
| 6,635,638 B2 | 10/2003 | Sui et al. |
| 2003/0144268 A1 | 7/2003 | Jiang et al. |

FOREIGN PATENT DOCUMENTS

| | | |
|---|---|---|
| DE | 2023514 | 12/1971 |
| EP | 0481429 B1 | 4/1992 |
| WO | 94/28902 A1 | 12/1994 |
| WO | 95/29900 A1 | 11/1995 |
| WO | 96/38438 A1 | 12/1996 |
| WO | 00/40561 A1 | 7/2000 |
| WO | 00/64897 A1 | 11/2000 |
| WO | WO 01/87882 * | 11/2001 |
| WO | 01/87882 A2 | 11/2001 |

OTHER PUBLICATIONS

Carniaux et al., Tetrahedron Letters, 38(17), 2997–3000, 1997.*
Boolell, M. et al.: "Sildenafil: an orally active type 5 cyclic GMP–specific phosphodiesterase inhibitor for the treatment of penile erectile dysfunction."; Int'l J. of Impotence Research (1996) 8, pp. 47–52.
Carniaux, J.F. et al.: "Synthesis of a Novel Fused Tricyclic Quinolone System via Oxidation of 1,2,3,4–Tetrahydro–β–Carbolines"; Tetrahedron Letters (1997), 38(17) 2997–3000.
Carter et al.: "Effect of the Selective Phosphodiesterase Type 5 Inhibitor Sildenafil on Erectile Function in the Anesthetized Dog"; The J. of Urology, vol. 160, Jul. 1998, pp. 242–246.
Thompson et al.: "Multiple Cyclic Nucleotide Phosphodiesterase Activities from Rat Brain"; Biochemistry, vol. 10, No. 2, 1971, pp. 311–316.
U.S. patent application Ser. No. 10/638,901, Ortho–McNeil Pharmaceutical, Inc.

* cited by examiner

Primary Examiner—Fiona T. Powers

(57) ABSTRACT

The invention relates to novel 2,4-dihydro-pyrrolo[3,4-b]quinolin-9-one derivatives of the formula (I) and (IV):

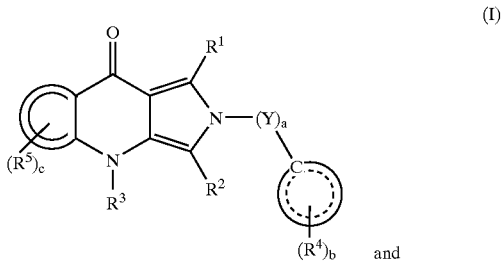

(I)

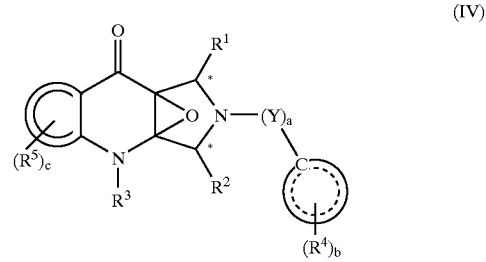

(IV)

wherein all variables are as herein defined, pharmaceutical compositions containing the compounds and their use for the treatment of sexual dysfunction.

22 Claims, No Drawings

SUBSTITUTED 2,4-DIHYDRO-PYRROLO[3,4-B]QUINOLIN-9-ONE DERIVATIVES USEFUL AS PHOSPHODIESTERASE INHIBITORS

CROSS REFERENCE TO RELATED APPLICATION

This application claims priority from U.S. Provisional Application Ser. No. 60/389,904, filed on Jun. 19, 2002, the contents of which are hereby incorporated by reference.

FIELD OF THE INVENTION

The invention relates to novel 2,4-dihydro-pyrrolo[3,4-b]quinolin-9-one derivatives, intermediates used in the preparation of, synthesis of and pharmaceutical compositions containing the derivatives and their use for the treatment of sexual dysfunction. The compounds of the present invention are phosphodiesterase inhibitors useful for the treatment of sexual dysfunction, more particularly male erectile dysfunction.

BACKGROUND OF THE INVENTION

Erectile dysfunction (ED) is defined as the inability to achieve or maintain an erection sufficiently rigid for satisfactory sexual intercourse. Currently it is estimated that approximately 7–8% of the male population suffer from some degree of ED, the equivalent of at least 20 million men in the United States alone. Since the likelihood of ED increases with age, it is projected that the incidence of this condition will rise in the future as the average age of the population increases.

Male erectile dysfunction may be the consequence of psychogenic and/or organic factors. Although ED is multifactorial, certain sub-groups within the male population are more likely to present with the symptoms of the disorder. In particular, patients with diabetes, hypertension, heart disease and multiple sclerosis have a particularly high prevalence of ED. In addition, patients who take certain classes of drugs such as antihypertensives, antidepressants, sedatives and anxiolytics are more prone to suffer from ED.

Treatments for ED include a variety of pharmacologic agents, vacuum devices and penile prostheses. Among the pharmacologic agents, papaverine, phentolamine, and alprostadil are currently used in practice. These agents are only effective after direct intracavernosal or intraurethral injection, and are associated with side effects such as priapism, fibrosis, penile pain and hematoma at the injection site. Vacuum devices are a noninasive alternative treatment for ED. These devices produce an erection by creating a negative pressure around the shaft of the penis resulting in an increased blood flow into the corpus cavernosum via passive arterial dilation. Although this form of therapy is frequently successful in ED of organic origin, complaints include the lack of spontaneity and the time involved in using a mechanical device, and the difficulty and discomfort with ejaculation. A variety of semi-rigid or inflatable penile prostheses have been used with some success, particularly in diabetic men. These devices are generally considered when other treatment options have failed, and are associated with an increased risk of infection and ischemia.

Recently, the phosphodiesterase V (PDEV) inhibitor, sildenafil (Viagra®) was approved by the FDA as an orally effective medication for the treatment of ED. Sildenafil, 5-[2-ethoxy-5-(4-methylpiperazin-1-ylsulphonyl)phenyl]-1-methyl-3-n-propyl-6,7-dihydro-1H-pyrazolo[4,3-d]pyrimidin-7-one and a number of related analogs and their use as antianginal agents are described in U.S. Pat. Nos. 5,250,534 and 5,346,901. The use of sildenafil and related analogs for treating male erectile dysfunction is described in PCT International Application Publication No. WO 94128902, published Dec. 22, 1994. In clinical studies, the drug improved sexual function in about 70% of the men who suffer from ED of psychogenic or organic etiology. However, the drug showed less dramatic efficacy in patients who had undergone a radical prostatectomy, with improved erections in 43% of patients who took sildenafil versus 15% on placebo. In addition, the use of sildenafil is associated with several undesirable side effects including headache, flushing and disrupted color vision which result from non-selective effects on a variety of tissues. In spite of these shortcomings, the drug is viewed by patients as preferable to other treatments which involve the introduction of medication directly into the penis via injection, the use of an external device or a surgical procedure.

Sexually stimulated penile erection results from a complex interplay of physiological processes involving the central nervous system, the peripheral nervous system and the smooth muscle. Specifically, release of nitric oxide from the non-adrenergic, non-cholinergic nerves and endothelium activates guanylyl cyclase and increases intracellular cGMP levels within the corpus cavernosum. The increase in intracellular cGMP reduces intracellular calcium levels, resulting in trabecular smooth muscle relaxation, which in turn, results in corporal volume expansion and compression of the sub-tunical venules leading to penile erection.

PDEV has been found in human platelets and vascular smooth muscle, suggesting a role for this enzyme in the regulation of intracellular concentrations of cGMP in cardiovascular tissue. In fact, inhibitors of PDEV have been shown to produce endothelial-dependent vasorelaxation by potentiating the increases in intracellular cGMP induced by nitric oxide. Moreover, PDEV inhibitors selectively lower the pulmonary arterial pressure in animal models of congestive heart failure and pulmonary hypertension. Hence in addition to their utility in ED, PDEV inhibitors would likely be of therapeutic benefit in conditions like heart failure, pulmonary hypertension and angina.

Agents that increase the concentration of cGMP in penile tissue, either through enhanced release or reduced breakdown of cGMP, are expected to be effective treatments for ED. The intracellular levels of cGMP are regulated by the enzymes involved in its formation and degradation, namely the guanylate cyclases and the cyclic nucleotide phosphodiesterases (PDEs). To date, at least nine families of mammalian PDEs have been described, five of which are capable of hydrolyzing the active, cGMP, to the inactive, GMP, under physiological conditions (PDEs I, II, V, VI, and IX). PDE V is the predominant isoform in human corpus cavernosum. Inhibitors of PDEV, therefore, would be expected to increase the concentration of cGMP in the corpus cavernosum and enhance the duration and frequency of penile erection.

Additionally, selective PDE inhibitors are known to be useful in the treatment of various disorders and conditions including male erectile dysfunction (ED), female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications.

Accordingly, it is an object of the invention to identify compounds which increase the concentration of cGMP in penile tissue through the inhibition of phosphodiesterases, specifically PDEV. It is another object of the invention to identify compounds which are useful for the treatment of sexual dysfunction, particularly erectile dysfunction and/or impotence in male animals and sexual dysfunction in female animals. Still another object of the invention is to identify methods for treating sexual dysfunction, especially erectile dysfunction, using the compounds of the present invention.

It is another object of the invention to identify compounds which are useful for the treatment of conditions of disorders mediated by PDEV, such as male erectile dysfunction, female sexual dysfunction, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication or diabetic complications.

We now describe a series of 2,4-dihydro-pyrrolo[3,4-b]quinolin-9-one derivatives with the ability to inhibit phosphodiesterase type V in enzyme assays.

SUMMARY OF THE INVENTION

The present invention provides novel 2,4-dihydro-pyrrolo[3,4-b]quinolin-9-one derivative compounds useful as phosphodiesterase inhibitors. More particularly, the present invention is directed to compounds of the general formula (I):

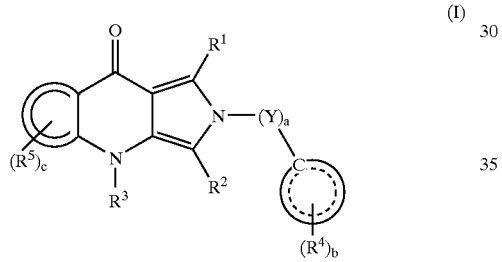

(I)

wherein
$R^1$ is selected from the group consisting of hydrogen, carboxy, —C(O)—$C_1$–$C_6$alkyl, —C(O)—$C_1$–$C_6$alkoxy, —C(O)—NH—$C_1$–$C_6$alkyl-$NH_2$, —C(O)NH—$C_1$–$C_6$alkyl-$NHR^A$, —C(O)—NH—$C_1$–$C_6$alkyl-$N(R^A)_2$, —C(O)—$NH_2$, —C(O)—$NHR^A$, —C(O)—$N(R^A)_2$, —$C_1$–$C_6$alkyl-$NH_2$, —$C_1$–$C_6$alkyl-$NHR^A$, —$C_1$–$C_6$alkyl-$N(R^A)_2$, —NH—$C_1$–$C_6$alkyl-$N(R^A)_2$;
where each $R^A$ is independently selected from the group consisting of $C_1$–$C_6$alkyl, aryl, $C_1$–$C_6$aralkyl and heteroaryl, where the aryl, aralkyl or heteroaryl may be optionally substituted with one to three $R^B$;
where each $R^B$ is independently selected from the group consisting of halogen, nitro, cyano, $C_1$–$C_6$alkyl, $C_1$–$C_6$alkoxy, $C_1$–$C_6$alkylcarbonyl, carboxy$C_1$–$C_6$alkyl, $C_1$–$C_6$alkylsulfonyl, trifluoromethyl, amino, di($C_1$–$C_6$alkyl)amino, acetylamino, carboxy$C_1$–$C_6$alkylcarbonylamino, hydroxy$C_1$–$C_6$alkylamino, $NHR^A$ and $N(R^A)_2$;
$R^2$ is selected from the group consisting of $C_5$–$C_{10}$alkyl (optionally substituted with one to three substituents independently selected from halogen, hydroxy, nitro, amino, $NHR^A$ or $N(R^A)_2$), aryl (optionally substituted with one to three substituents independently selected from $R^C$), cycloalkyl (optionally substituted with one to three substituents independently selected from $R^A$), heteroaryl (optionally substituted with one to three substituents independently selected from $R^C$), and heterocycloalkyl (optionally substituted with one to three substituents independently selected from $R^C$);
where $R^C$ is selected from the group consisting of halogen, nitro, cyano, $C_1$–$C_6$alkyl, $C_1$–$C_6$alkoxy, trifluoromethyl, trifluoromethoxy, $NH_2$, $NH(C_1$–$C_6$alkyl) and $N(C_1$–$C_6$alkyl)_2$;
$R^3$ is selected from the group consisting of hydrogen, $C_1$–$C_6$alkyl, $C_1$–$C_6$alkylcarbonyl, $C_2$–$C_6$alkenylcarbonyl and $C_2$–$C_6$alkynylcarbonyl;
b is an integer from 0 to 4;
$R^4$ is independently selected from the group consisting of halogen, hydroxy, carboxy, oxo, nitro, $C_1$–$C_6$alkyl, $C_1$–$C_6$alkoxy, $C_1$–$C_6$alkoxycarbonyl, trifluoromethyl, phenyl (wherein the phenyl group may be optionally substituted with one to three substituents independently selected from $R^D$), phenylsulfonyl, naphthyl, $C_1$–$C_6$aralkyl, —O-aralkyl, (wherein the aralkyl group may be optionally substituted with one to three substituents independently selected from $R^D$), heteroaryl (wherein the heteroaryl may be optionally substituted with one to three substituents independently selected from $R^D$), heterocycloalkyl, $NH_2$, $NHR^A$, $N(R^A)_2$,

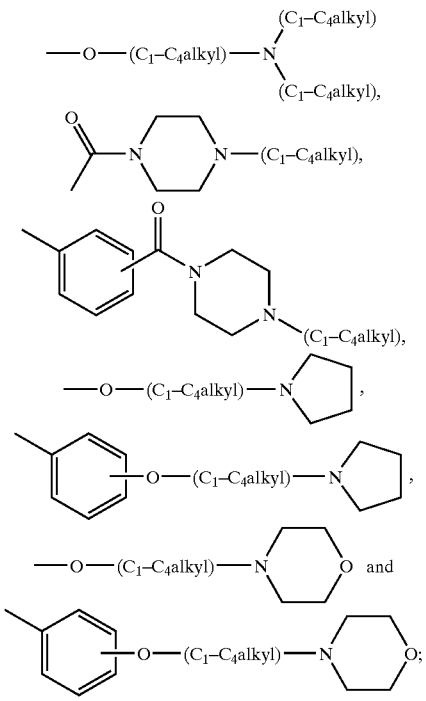

where each $R^D$ is independently selected from the group consisting of halogen, hydroxy, carboxy, oxo, $C_1$–$C_4$alkyl, $C_{1-4}$alkylthio, hydroxy$C_{1-4}$alkyl, $C_1$–$C_4$alkoxy, $C_1$–$C_4$alkyoxycarbonyl, $C_1$–$C_4$alkylcarbonyl, trifluoromethyl, trifluoromethoxy, $NH_2$, $NHR^A$, $N(R^A)_2$, $C(O)N(R^A)_2$, acetylamino, nitro, cyano, formyl, $C_1$–$C_6$alkylsulfonyl, carboxy$C_1$–$C_6$alkyl and aralkyl;
c is an integer from 0 to 4;
$R^5$ is independently selected from the group consisting of halogen, nitro, hydroxy, $C_1$–$C_6$alkyl, $C_1$–$C_6$alkoxy, —$NH_2$, —$NHR^A$, —$N(R^A)_2$, —$OR^A$, —$C(O)NH_2$, —$C(O)NHR^A$, —$C(O)N(R^A)_2$, —$NHC(O)R^A$, —SO$_2$NHR$^A$, —SO$_2$N(R$^A$)2, where R$^A$ is as defined above, phenyl (optionally substituted with one to three substituents independently selected from R$^B$), heteroaryl (optionally substituted with one to three substituents independently selected from R$^B$) and heterocycloalkyl (optionally substituted with one to three substituents independently selected from R$^B$);

a is an integer from 0 to 1;

Y selected from the group consisting of —C$_1$–C$_6$alkyl-, —C(O)—, —(C$_1$–C$_6$alkyl)carbonyl-, —(C$_2$–C$_6$alkenyl)carbonyl-, —(C$_2$–C$_6$alkynyl)carbonyl-, -carbonyl(C$_1$–C$_6$alkyl)-, -carbonyl(C$_2$–C$_6$alkenyl)-, —C(O)O—(C$_1$–C$_6$alkyl)-, —C(S)—, —SO$_2$—, —(C$_1$–C$_6$alkyl)sulfonyl-, -sulfonyl(C$_1$–C$_6$alkyl)-, —C(O)NH—, —C(O)NH—(C$_1$–C$_6$alkyl)-, —C(O)(C$_3$–C$_7$cycloalkyl)- and —C$_3$–C$_7$cycloalkyl)-C(O)—;

is selected from the group consisting phenyl, furyl, thienyl and pyrrol;

is selected from the group consisting of aryl, heteroaryl, cycloalkyl and heterocycloalkyl;

proved that when R$^1$ is hydrogen, R$^3$ is hydrogen, b is 0, c is 0, a is 1, Y is —CH$_2$—,

is phenyl and

is phenyl, then R$^2$ is not trimethoxyphenyl (i.e. not 2-benzyl-3-(3,4,5-trimethoxy-phenyl)-2,4-dihydro-pyrrolo[3,4-b]quinolin-9-one and other compounds where the three methoxy groups are substituted on the phenyl substituent in a different pattern);

or a pharmaceutically acceptable salt thereof.

The present invention is further directed to compounds of the general formula (IV)

(IV)

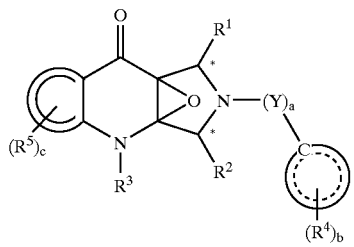

wherein

R$^1$ is selected from the group consisting of hydrogen, carboxy, —C(O)—C$_1$–C$_6$alkyl, —C(O)—C$_1$–C$_6$alkoxy, —C(O)—NH—C$_1$–C$_6$alkyl-NH$_2$, —C(O)—NH—C$_1$–C$_6$alkyl-NHR$^A$, —C(O)—NH—C$_1$–C$_6$alkyl-N(R$^A$)$_2$, —C(O)—NH$_2$, —C(O)—NHR$^A$, —C(O)—N(R$^A$)$_2$, —C$_1$–C$_6$alkyl-NH$_2$, —C$_1$–C$_6$alkyl-NHR$^A$, —C$_1$–C$_6$alkyl-N(R$^A$)$_2$, —NH—C$_1$–C$_6$alkyl-N(R$^A$)$_2$;

where each R$^A$ is independently selected from the group consisting of C$_1$–C$_6$alkyl, aryl, C$_1$–C$_6$aralkyl and heteroaryl, where the aryl, aralkyl or heteroaryl may be optionally substituted with one to three R$^B$;

where each R$^B$ is independently selected from the group consisting of halogen, nitro, cyano, C$_1$–C$_6$alkyl, C$_1$–C$_6$alkoxy, C$_1$–C$_6$alkylcarbonyl, carboxyC$_1$–C$_6$alkyl, C$_1$–C$_6$alkylsulfonyl, trifluoromethyl, amino, di(C$_1$–C$_6$alkyl)amino, acetylamino, carboxyC$_1$–C$_6$alkylcarbonylamino, hydroxyC$_1$–C$_6$alkylamino, NHR$^A$ and N(R$^A$)$_2$;

R$^2$ is selected from the group consisting of C$_5$–C$_{10}$alkyl (optionally substituted with one to three substituents independently selected from halogen, hydroxy, nitro, amino, NHR$^A$ or N(R$^A$)$_2$), aryl (optionally substituted with one to three substituents independently selected from R$^C$), cycloalkyl (optionally substituted with one to three substituents independently selected from R$^A$), heteroaryl (optionally substituted with one to three substituents independently selected from R$^C$), and heterocycloalkyl (optionally substituted with one to three substituents independently selected from R$^C$);

where R$^C$ is selected from the group consisting of halogen, nitro, cyano, C$_1$–C$_6$alkyl, C$_1$–C$_6$alkoxy, trifluoromethyl, trifluoromethoxy, NH$_2$, NH(C$_1$–C$_6$alkyl) and N(C$_1$–C$_6$alkyl)$_2$;

R$^3$ is selected from the group consisting of hydrogen, C$_1$–C$_6$alkyl, C$_1$–C$_6$alkylcarbonyl, C$_2$–C$_6$alkenylcarbonyl and C$_2$–C$_6$alkynylcarbonyl;

b is an integer from 0 to 4;

R$^4$ is independently selected from the group consisting of halogen, hydroxy, carboxy, oxo, nitro, C$_1$–C$_6$alkyl, C$_1$–C$_6$alkoxy, C$_1$–C$_6$alkoxycarbonyl, trifluoromethyl, phenyl (wherein the phenyl group may be optionally substituted with one to three substituents independently selected from R$^D$), phenylsulfonyl, naphthyl, C$_1$–C$_6$aralkyl, —O-aralkyl, (wherein the aralkyl group may be optionally substituted with one to three substituents independently selected from R$^D$), heteroaryl (wherein the heteroaryl may be optionally substituted with one to three substituents independently selected from R$^D$), heterocycloalkyl, NH$_2$, NHR$^A$, N(R$^A$)$_2$,

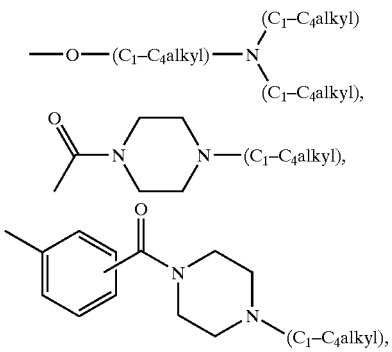

-continued

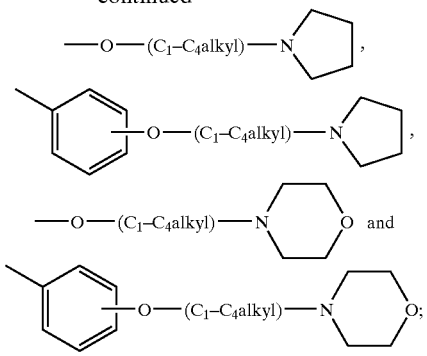

where each $R^D$ is independently selected from the group consisting of halogen, hydroxy, carboxy, oxo, $C_1$–$C_4$alkyl, $C_{1-4}$alkylthio, hydroxy$C_{1-4}$alkyl, $C_1$–$C_4$alkoxy, $C_1$–$C_4$alkyoxycarbonyl, $C_1$–$C_4$alkylcarbonyl, trifluoromethyl, trifluoromethoxy, $NH_2$, $NHR^A$, $N(R^A)_2$, $C(O)N(R^A)_2$, acetylamino, nitro, cyano, formyl, $C_1$–$C_6$alkylsulfonyl, carboxy$C_1$–$C_6$alkyl and aralkyl;

c is an integer from 0 to 4;

$R^5$ is independently selected from the group consisting of halogen, nitro, hydroxy, $C_1$–$C_6$alkyl, $C_1$–$C_6$alkoxy, $-NH_2$, $-NHR^A$, $-N(R^A)_2$, $-OR^A$, $-C(O)NH_2$, $-C(O)NHR^A$, $-C(O)N(R^A)_2$, $-NHC(O)R^A$, $-SO_2NHR^A$, $-SO_2N(R^A)_2$, where $R^A$ is as defined above, phenyl (optionally substituted with one to three substituents independently selected from $R^B$), heteroaryl (optionally substituted with one to three substituents independently selected from $R^B$) and heterocycloalkyl (optionally substituted with one to three substituents independently selected from $R^B$);

a is an integer from 0 to 1;

Y selected from the group consisting of $-C_1$–$C_6$alkyl-, $-C(O)-$, $-(C_1$–$C_6$alkyl)carbonyl-, $-(C_2$–$C_6$alkenyl)carbonyl-, $-(C_2$–$C_6$alkynyl)carbonyl-, -carbonyl($C_1$–$C_6$alkyl)-, -carbonyl($C_2$–$C_6$alkenyl), $-C(O)O-(C_1$–$C_6$alkyl), $-C(S)-$, $-SO_2-$, $-(C_1$–$C_6$alkyl)sulfonyl-, -sulfonyl($C_1$–$C_6$alkyl)-, $-C(O)NH-$, $-C(O)NH-(C_1$–$C_6$alkyl)-, $-C(O)(C_3$–$C_7$cycloalkyl)- and $C_3$–$C_7$cycloalkyl)$-C(O)-$;

is selected from the group consisting phenyl, furyl, thienyl and pyrrolyl;

is selected from the group consisting of aryl, heteroaryl, cycloalkyl and heterocycloalkyl;

or a pharmaceutically acceptable salt thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating a condition selected from the group consisting of male erectile dysfunction (ED), impotence, female sexual dysfunction, female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of any of the compounds or pharmaceutical compositions described above.

An example of the invention is a method for increasing the concentration of cGMP in penile tissue through the inhibition of phosphodiesterases, specifically PDEV, in a male subject in need thereof comprising administering to the subject an effective amount of any of the compounds or pharmaceutical compositions described above.

Further exemplifying the invention is a method of producing endothelial-dependent vasorelaxation by potentiating the increases in intracellular cGMP induced by nitric oxide in a subject in need thereof comprising administering to the subject an effective amount of any of the compounds or pharmaceutical compositions described above.

An example of the invention is the use of any of the compounds described above in the preparation of a medicament for (a) treating sexual dysfunction, especially male erectile dysfunction, (b) treating impotence, (c) increasing the concentration of cGMP in penile tissue through inhibition of phosphodiesterase, especially PDEV and/or (d) treating a condition selected from the group consisting of premature labor, dysmenorrhea, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication and diabetic complications in a subject in need thereof.

DETAILED DESCRIPTION OF THE INVENTION

The present invention provides novel 2,4-dihydro-pyrrolo [3,4-b]quinolin-9-one derivatives useful for the treatment of sexual dysfunction, particularly male erectile dysfunction (ED). Although the compounds of the present invention are useful primarily for the treatment of male sexual dysfunction or erectile dysfunction, they may also be useful for the treatment of female sexual dysfunction, for example female sexual arousal dysfunction, female sexual dysfunction related to blood flow and nitric oxide production in the tissue of the vagina and clitoris, and for the treatment of premature labor and dysmenorrhea.

More particularly, the compounds of the present invention are of the

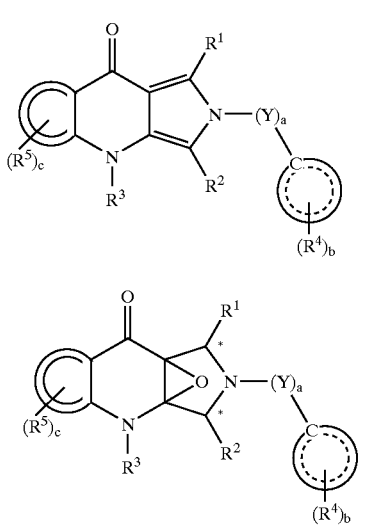

(I)

or (IV)

wherein all variables are as defined above, or a pharmaceutically acceptable salt thereof. The compounds of formula (I) are useful for the treatment of disorders mediated by the PDEV receptor, including, but not limited to, sexual dysfunction. The compounds of formula (IV) are useful as intermediates in the preparation of compounds of formula (I).

Preferably, $R^1$ is hydrogen.

In an embodiment of the present invention $R^2$ is selected from the group consisting of phenyl (optionally substituted with one to two substituent selected from halogen, nitro, cyano, $C_1$–$C_3$alkyl, $C_1$–$C_3$alkoxy, trifluoromethyl, trifluoromethoxy, $NH_2$, $NH(C_1$–$C_3$alkyl) or $N(C_1$–$C_3$alkyl)$_2$), heteroaryl and heterocycloalkyl. Preferably, $R^2$ is selected from the group consisting of 3,4-methylenedioxyphenyl, 3,4-dimethoxyphenyl, 5-(2,3-dihydrobenzofuryl), 3,4-dihydrobenzo-[1,4]-dioxin-6-yl, 5-benzofuryl, 5-indanyl and 3-thienyl. More preferably, $R^2$ is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl. Most preferably, $R^2$ is selected from the group consisting of 3,4-methylenedioxyphenyl, and 5-(2,3-dihydrobenzofuryl).

Preferably, $R^3$ is selected from the group consisting of hydrogen and $C_1$–$C_4$alkyl. More preferably, $R^3$ is selected from the group consisting of hydrogen and methyl. Most preferably, $R^3$ is hydrogen.

Preferably, b is an integer from 0 to 4. More preferably b is in integer from 0 to 1.

In an embodiment of the present invention, $R^4$ is selected from the group consisting of halogen, hydroxy, carboxy, oxo, $C_1$–$C_3$alkyl, $C_1$–$C_3$alkoxy, $C_1$–$C_3$alkoxycarbonyl, phenyl (wherein the phenyl may be optionally substituted with one to two substituents selected from hydroxy, carboxy, $C_1$–$C_4$alkyl, $C_{1-4}$alkylthio, hydroxy$C_{1-4}$alkyl, $C_1$–$C_4$alkoxy, $C_1$–$C_4$alkyoxycarbonyl, $C(O)N(R^A)_2$, trifluoromethyl, trifluoromethoxy, amino, $(C_{1-4}$alkyl)amino, di$(C_{1-4}$alkyl) amino, nitro, cyano or formyl), O-aralkyl, heteroaryl (wherein the heteroaryl may be optionally substituted with one to two substituents selected from hydroxy, carboxy, oxo, $C_1$–$C_3$alkyl, $C_1$–$C_3$alkoxy, $C_1$–$C_3$alkyoxycarbonyl, C(O)N $(R^A)_2$, trifluoromethyl, trifluoromethoxy, amino, nitro, $C_1$–$C_3$alkylcarbonyl or $C_{1-4}$aralkyl), heterocycloalkyl,

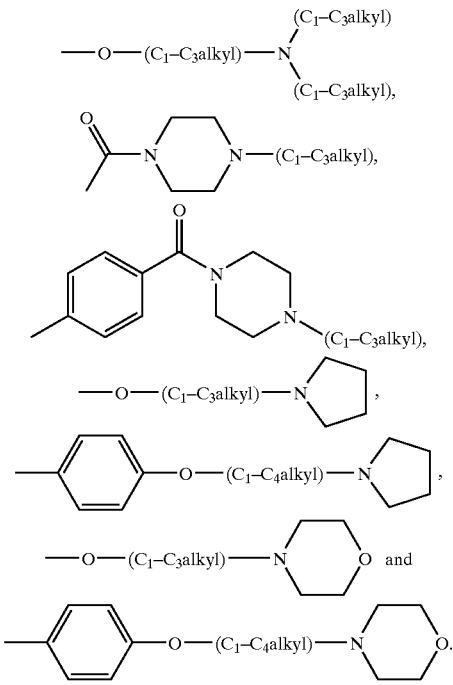

Preferably, $R^4$ is selected from the group consisting of bromo, hydroxy, carboxy, oxo, methyl, phenyl, 4-hydroxyphenyl, 3-hydroxymethylphenyl, 4-hydroxymethylphenyl, 4-carboxyphenyl, 4-methylphenyl, 4-methoxyphenyl, 3,4-dimethoxyphenyl, 4-methoxycarbonyl, 4-methoxycarbonylphenyl, 3-trifluoromethylphenyl, 4-cyanophenyl, 4-aminophenyl, 4-dimethylaminophenyl, 3-nitrophenyl, 4-nitrophenyl, 4-formylphenyl, 4-methylthiophenyl, benzyloxy, 2-pyridinyl, 3-pyridinyl, 4-pyridinyl, N-oxy-2-pyridinyl, 3-thienyl, 2-furyl, 1-imidazolyl, 5(1-benzyl-2-methylimidazolyl), 5-(1,2-dimethylimidazolyl), 5-(1-methylimidazolyl), 5(1-benzylimidazolyl), 3,4-methylenedioxyphenyl,

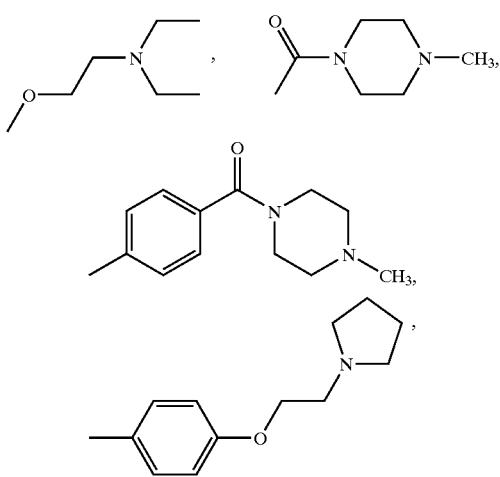

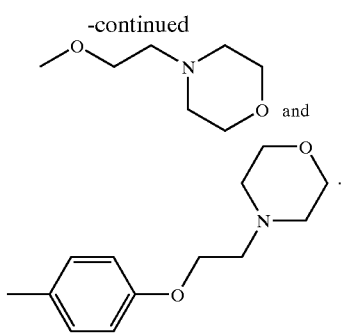

More preferably, $R^4$ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, 2-furyl, 3-thienyl, N-oxo-2-pyridinyl, 1-imidazolyl, 5-(1-benzyl-2-methylimidazolyl), 5-(1,2-dimethylimidazolyl), 3,4-methylenedioxyphenyl,

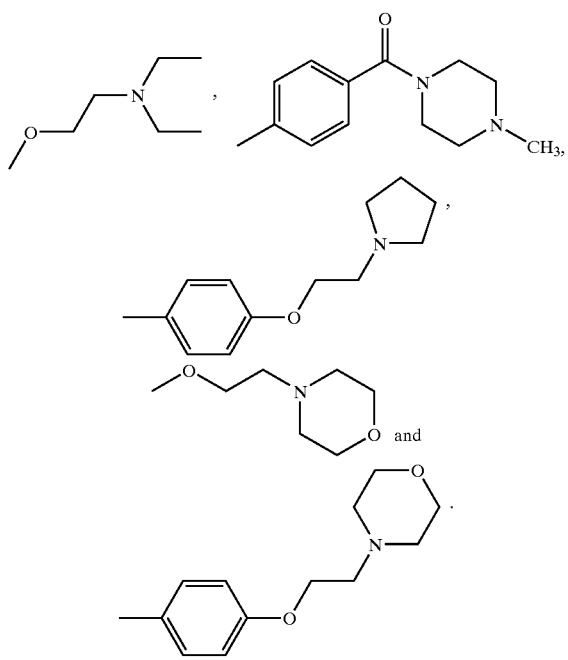

More preferably still, $R^4$ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, N-oxo-2-pyridinyl, 3-thienyl, 2-furyl, 1-imidazolyl, 5-(1-benzyl-2-methylimidazolyl), 5-(1,2-dimethylimidazolyl), 3,4-methylenedioxyphenyl,

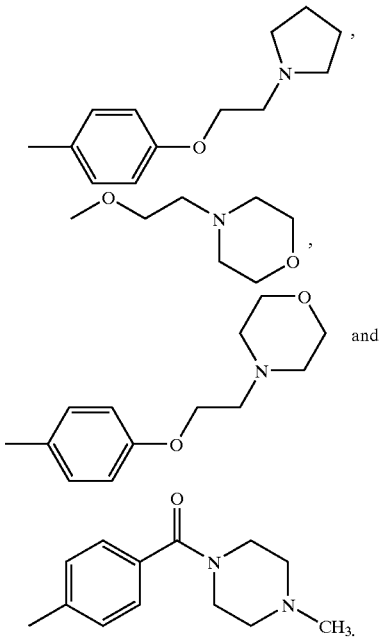

More preferably still, R4 is selected from the group consisting of 6-hydroxy, 4-carboxy, phenyl, 4-hydroxyphenyl, 3-hydroxymethylphenyl, 4-methylphenyl, 4-methylthiophenyl, 4-methoxyphenyl, 3,4-dimethoxyphenyl, 4-methoxycarbonyl, 3-trifluoromethylphenyl, 3-nitrophenyl, 4-nitrophenyl, 2-pyridinyl, 3-pyridinyl, 4-pyridinyl, N-oxo-2-pyridinyl, 3-thienyl, 5-(1-benzyl-2-methylimidazolyl), 5-(1,2-dimethylimidazolyl),

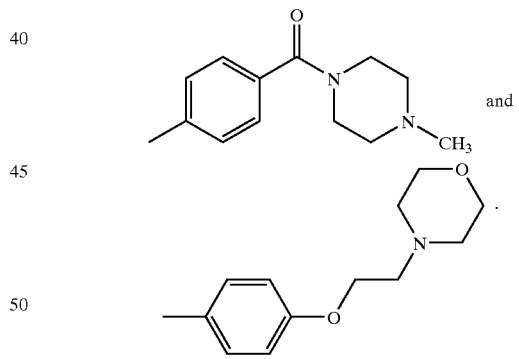

Most preferably, $R^4$ is selected from the group consisting of hydroxy, 4-methylphenyl, 4-methoxyphenyl, 3,4-dimethoxyphenyl, 4-methoxycarbonyl, 3-trifluoromethylphenyl, 4-nitrophenyl, 2-pyridinyl, 3-pyridinyl,

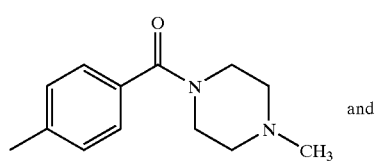

-continued

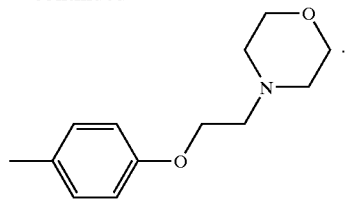

In a preferred embodiment c is 0.

In an embodiment of the present invention, Y is selected from the group consisting of —$C_1$-$C_4$alkyl-, —C(S)—, —C(O)—, —C(O)O—($C_1$-$C_4$alkyl)-, —C(O)—($C_1$-$C_4$alkyl)-, —C(O)—($C_2$-$C_4$alkenyl)-, C(O)—($C_3$-$C_7$cycloalkyl)- and —C(O)NH—($C_1$-$C_3$alkyl)-. Preferably, Y is selected from the group consisting of —$CH_2$—, —C(S)—, —C(O)—, —C(O)O—$CH_2$—, —C(O)—$CH_2CH_2$—, —C(O)—CH=CH—, —C(O)NH—$CH_2$—, —C(O)-cyclopropyl and —C(O)$CH_2$—. More preferably, Y is selected from the group consisting of —C(O)—, —C(O)O—$CH_2$—, —C(O)$CH_2CH_2$—, —C(O)—CH=CH—, and —C(O)-cyclopropyl. More preferably still, Y is selected from the group consisting of —C(O)—, —C(O)O—$CH_2$— and —C(O)—CH=CH—. Most preferably, Y is selected from the group consisting of —C(O)— and —C(O)O—$CH_2$—;

Preferably

is phenyl;

In an embodiment of the present invention,

is selected from the group consisting of phenyl, heteroaryl and heterocycloalkyl. Preferably,

is selected from the group consisting of phenyl, 2-furyl, 2-benzo(b)furyl, 2-pyrimidinyl, 2-pyridinyl, 3-pyridinyl, 4-pyridinyl, 1-imidazolyl, 2-imidazolyl, 2-thiazolyl, and 2oxa-bicyclo[2.2.1]heptanyl. More preferably

is selected from the group consisting of phenyl, 2-furyl, 2-benzo(b)furyl, 2-pyrimidinyl, 2-pyridinyl, 3-pyridinyl, 4-pyridinyl and 2-thiazolyl. Most preferably,

is selected from the group consisting of 2-furyl, 2-benzo(b)furyl, 4-pyridinyl, 2-pyrimidinyl and 2-thiazolyl.

The term "halogen" shall include iodine, bromine, chlorine and fluorine.

The term "alkyl", whether used alone or as part of a substituent group, shall mean straight or branched chain alkanes of one to ten carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl and 2-methylpentyl. Similarly, alkenyl and alkynyl groups include straight and branched chain alkenes and alkynes having two to ten carbon atoms, or any number within this range.

The term "alkoxy" shall denote an oxygen ether radical of the above described straight or branched chain alkyl group. For example, alkoxy radicals include methoxy, ethoxy, n-propoxy, n-butoxy, sec-butoxy, tert-butoxy, and the like.

The term "aryl" indicates an aromatic group such as phenyl, naphthyl, and the like.

The term "aralkyl" denotes an alkyl group substituted with an aryl group For example, benzyl, phenylethyl, and the like. Similarly, the term "aralkenyl" denotes an alkenyl group substituted with an aryl group, for example phenylethylenyl, and the like.

The term "heteroaryl" as used herein represents a stable five or six membered monocyclic aromatic ring system containing one to three heteroatoms independently selected from N, O or S; and any nine or ten membered bicyclic aromatic ring system containing carbon atoms and one to four heteroatoms independently selected from N, O or S. The heteroaryl group may be attached at any heteroatom or carbon atom which results in the creation of a stable structure. Examples of heteroaryl groups include, but are not limited to pyridinyl, pyrimidinyl, thienyl, furyl, imidazolyl, isoxazolyl, oxazolyl, pyrazolyl, pyrazinyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl, isoquinolinyl, purinyl. Preferred heteroaryl groups include pyrimidinyl, pyridinyl, furyl, imidazolyl, benzofuryl and thiazolyl.

The term "cycloalkyl" as used herein represents a stable three to eight membered monocyclic ring structure consisting of saturated carbon atoms. Suitable examples include cyclopropyl, cyclobutyl, cydopentyl, cyclohexyl, cycloheptyl and cyclooctyl.

The term "heterocycloalkyl" represents a stable saturated or partially unsaturated, three to eight membered monocyclic ring structure containing carbon atoms and one to four, preferably one to two, heteroatoms independently selected from N, O or S; and any stable saturated, partially unsaturated or partially aromatic, nine to ten membered bicyclic ring system containing carbon atoms and one to four heteroatoms independently selected from N, O or S. The heterocycloalkyl may be attached at any carbon atom or heteroatom which results in the creation of a stable structure. Suitable examples of heterocycloalkyl groups include pyrrolidinyl, pyrazolidinyl, piperidinyl, piperazinyl, morpholinyl, dithianyl, trithianyl, dioxolanyl, dioxanyl, thiomorpholinyl, 3,4-methylenedioxyphenyl, 2,3-dihydrobenzofuryl, 2,3-dihydrobenzo-[1,4]-dioxin-6-yl, 2,3-dihydro-furo[2,3-b]pyridinyl, 1,2-methylenedioxy)cyclohexane, indanyl, 2-oxa-bicyclo[2.2.1]heptanyl, and the like. Preferred heterocycloalkyl groups include piperidinyl, pyrrolidinyl, morpholinyl, indanyl, 2-oxa-bicyclo[2.2.1]heptanyl, 3,4-methylenedioxyphenyl, 2,3-dihydrobenzofuryl and 2,3-dihydrobenzo-[1,4]-dioxin-6-yl.

As used herein, the notation "*" shall denote the presence of a stereogenic center.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. It is further intended that when b or c is >1, the corresponding $R^4$ or $R^5$ substituents may be the same or different.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$–$C_6$ alkylaminocarbonyl$C_1$–$C_6$alkyl" substituent refers to a group of the formula

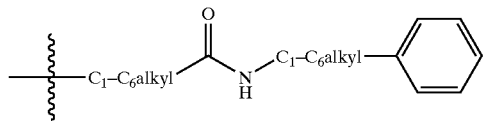

The term "sexual dysfunction" as used herein, includes male sexual dysfunction, male erectile dysfunction, impotence, female sexual dysfunction, female sexual arousal dysfunction and female sexual dysfunction related to blood flow and nitric oxide production in the tissues of the vagina and clitoris.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Abbreviations used in the specification, particularly the Schemes and Examples, are as follows:

| | |
|---|---|
| Cmpd # = | Compound Number |
| DCM = | Dichloromethane |
| DMF = | N,N'-Dimethylformamide |
| DMSO = | Dimethyl sulfoxide |
| EDTA = | Ethylenedinitrilotetracetic acid |
| HEPES = | 2-[4-(2-hydroxyethyl)-piperazinyl]-ethanesulfonic acid |
| HPLC = | High Pressure Liquid Chromatography |
| LCMS = | Liquid Chromatography Mass Spectroscopy |
| MeOH = | Methanol |
| mCPBA = | 3-Chloroperoxybenzoic Acid |
| PDE = | Phosphodiesterase |
| PDEV = | Phosphodiesterase Type V |
| PMSF = | Phenylmethanesulfonyl fluoride |
| t-BuOOH = | tert-Butyl hydroperoxide |
| THF = | Tetrahydrofuran |
| TLC = | Thin Layer Chromatography |
| Tris HCl = | Tris[hydroxymethyl]aminomethyl hydrochloride |

Compounds of formula (I) may be prepared from the corresponding pyrrolopyridinones according to the process outlined in Scheme 1.

Scheme 1

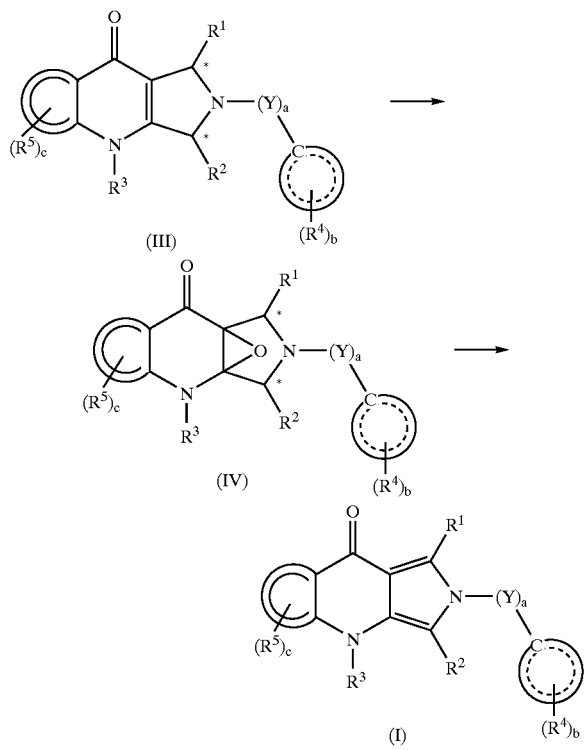

Accordingly, a suitably substituted compound of formula (III), a known compound or compound prepared by known methods, is reacted with an oxidizer such as mCPBA, $H_2O_2$, t-BuOOH, and the like, in an organic solvent such as dichloromethane, DMF, THF, MeOH, and the like, to yield the corresponding compound of formula (IV).

The compound of formula (IV) is reacted with an acid such as acetic acid, hydrochloric acid, sulfuric acid, phosphoric acid, and the like, to yield the corresponding compound of formula (I).

One skilled in the art will recognize that during the first step of the process outlined in Scheme 1 above, the oxidizer mCPBA will convert to 3-chloro-benzoic acid which will act like acetic acid during the second step of the process outlined in Scheme 1. The 3-chloro-benzoic acid will therefore convert the compound of formula (IV) into the compound of formula (I), thereby allowing for a one pot synthesis of the compound of formula (I). Further, one skilled in the art will recognize that when .the compound of formula (IV) is desired and mCPBA is used as the oxidizer, the process in Scheme 1 is monitored for the formation of the compound of formula (IV) and the compound of formula (I) by known methods, for example, by thin layer chromatography, HPLC or LCMS, and the reaction is quenched with a weak base such as $NaHCO_3$, $KH_2PO_4$, pyridine, and the like, to stop the reaction at an appropriate time (i.e. at a time when the amount of the compound of formula (IV) is maximized and when conversion of the compound of formula (IV) to the compound of formula (I) is minimized).

Compounds of formula (III) are known compounds or compounds which may be prepared by known methods, for example, as disclosed by Sui et al in WIPO publication WO 01/87882 published Nov. 22, 2001.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared by enantioselective synthesis, by resolution or from enantiomerically enriched reagents. The compounds may, for example, be resolved into their component enantiomers by standard techniques, such as the formation of diastereomeric pairs by salt formation with an optically active acid, such as (−)di-p-toluoyl-tartaric acid and/or (+)-di-p-toluoyl-l-tartaric acid followed by fractional crystallization and regeneration of the free base. The compounds may also be resolved by formation of diastereomeric esters, amides or amines, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds to treat sexual dysfunction can be determined according to the procedures described in Example 5, 6 and 7 herein.

The present invention therefore provides a method of treating sexual dysfunction, more particularly male erectile dysfunction in a subject in need thereof which comprises administering any of the compounds as defined herein in a quantity effective to treat ED. The compound may be administered to a patient by any conventional route of administration, including, but not limited to, intravenous, oral, subcutaneous, intramuscular, intradermal and parenteral. The quantity of the compound which is effective for treating ED is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating sexual dysfunction, more particularly male erectile dysfunction described in the present invention may also be carried out using a pharmaceutical composition comprising any of the compounds as defined herein and a pharmaceutically acceptable carrier. The pharmaceutical composition may contain between about 1 mg and 1000 mg, preferably about 1 to 200 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and mutilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of sexual dysfunction, more particularly male erectile dysfunction is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.1 mg/kg to about 3 mg/kg of body weight per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter. Unless otherwise indicated, $^1$H NMRs were run on a Bruker instrument.

EXAMPLE 1

3-(1,3-Benzodioxol-5-yl)-2,3-dihydro-2-phenylmethyl)-3a,9a-epoxy-1H-pyrrolo[3,4-b]quinolin-9-(4H)-one (Compound #1)

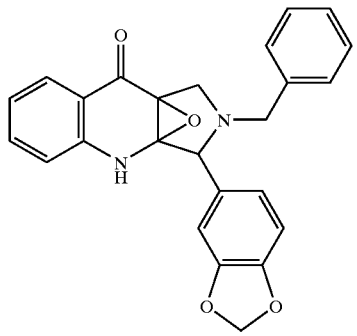

3-Benzo[1,3]dioxol-5-yl-2-benzyl-1,2,3,4-tetrahydro-pyrrolo[3,4-b]quinolin-9-one, prepared as in WO 01/87882, Example 3, page 45, (39.6 mg, 0.1 mmol) in CH$_2$Cl$_2$ (5 mL) was added to a solution of mCPBA (19 mg, 0.11 mmol) in CH$_2$Cl$_2$ (5 mL). The reaction mixture was then stirred in at room temperature for 1 h. The product was isolated by preparative TLC (5% MeOH/CH$_2$Cl$_2$) to yield the title compound as a yellow solid.

$^1$H NMR 300 MHz (CD$_3$OD) δ 3.94 (m, 2H), 4.20 (m, 2H), 5.05 (s, 1H), 6.02 (d, 2H), 6.91~8.7 (m, 12H). MS (m/z) MH$^+$ (413), MH$^-$ (411).

EXAMPLE 2

2-Benzyl-3-(2,3-dihydro-benzofuran-5-yl)-2,4-dihydro-pyrrolo[3,4-b]quinolin-9-one (Compound #2)

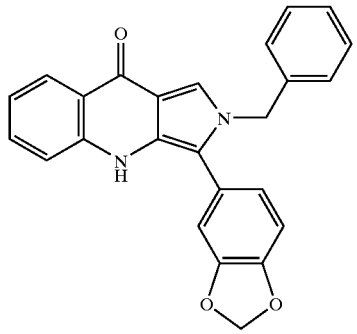

3-Benzo[1,3]dioxol-5-yl-2-benzyl-1,2,3,4-tetrahydro-pyrrolo[3,4-b]quinolin-9-one, prepared as in WO 01/87882, Example 3, page 45, (39.6 mg, 0.1 mmol) in a mixture of CH$_2$Cl$_2$ (4 mL) and DMF (1 mL) was stirred with a solution of mCPBA (26 mg, 0.15 mmol) in CH$_2$Cl$_2$ (2 mL) at room temperature for 72 h. The product was isolated by preparative TLC (2.5% MeOH/CH$_2$Cl$_2$, Rf=0.72) to yield the title compound as a yellow solid.

$^1$H NMR 300 MHz (CD$_3$OD) δ 5.35 (s, 2H), 6.12 (s, 2H), 6.78~7.60 (m, 11H), 7.75 (s, 1H), 8.28 (d, 1H). MS (m/z) MH$^+$ (395), MH$^-$ (393).

EXAMPLE 3

2-Benzyl-3-(2,3-dihydro-benzofuran-5-yl)-2,4-dihydro-pyrrolo[3,4-b]quinolin-9-one (Compound #2)

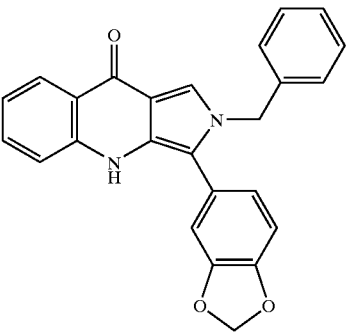

The title compound was prepared by stirring 3-(1,3-benzodioxol-5-yl)-2,3-dihydro-2-(phenylmethyl)-3a,9a-epoxy-1H-pyrrolo[3,4-b]quinolin-9-(4H)-one, prepared as in Example 1, with HCl (2 drops of 1N aqueous solution) in a mixture of CH$_2$Cl$_2$ and DMF (4:1) for 72 hours at room temperature.

EXAMPLE 4

3-(2,3-Dihydro-benzofuran-5-yl)-2-(1R-1-naphthalen-1-yl-ethyl)-2,4-dihydro-pyrrolo[3,4-b]quinolin-9-one (Compound #3)

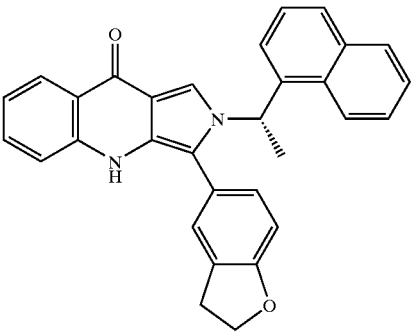

3-(2,3-Dihydro-benzofuran-5-yl)-2-(1R-1-naphthalen-1-yl-ethyl)-1,2,3,4-tetrahydro-1R-9H-pyrrolo[3,4-b]quinolin-9-one, prepared as in WO 01/87882, Example 67, Steps A through D, pages 89–91, (0.19 g, 0.415 mmol) in DCM (15 mL) was stirred with mCPBA (0.102 g, 0.456 mmol) for 7 hours at 25° C. Hydrogen chloride (0.2 mL, 2.0 M in ether) and DCM (5 mL) were added to the reaction mixture, which was then stirred at room temperature for 16 hours. HCl (0.1 mL, 1.0 M in H$_2$O) was added and the reaction mixture was stirred at 25° C. for another 16 hours. The product was isolated by preparative TLC (1% MeOH/DCM) to yield the title compound as a yellow solid.

$^1$H NMR 300 MHz (CDCl$_3$) δ 1.95 (d, 6H, J=8 Hz), 2.81~3.05 (m, 2H), 4.48 (m, 2H), 6.15 (m, 1H), 6.52~8.48 (sets of m, 14H) MS (m/z) MH$^+$ (457), 479 (MNa$^+$), 2MNa$^+$ (935), MH$^-$ (455).

EXAMPLE 5

In Vitro Testing
Cyclic Nucleotide Phosphodiesterase (PDE) Assay

PDEV Isolation

PDEV was isolated from rabbit and human tissues according to the protocol described by Boolell et al. (Boolell, M., Allen, M. J., Ballard, S. A., Ge[o-Attee, S., Muirhead, G. J., Naylor, A. M., Osterdoh, I. H., and Gingell, C) in *International Journal of Impotence Research* 1996 8, 47–52 with minor modifications.

Briefly, rabbit or human tissues were homogenized in an ice-cold buffer solution containing 20 mM HEPES (pH 7.2), 0.25M sucrose, 1 mM EDTA, and 1 mM phenylmethylsulphonyl fluoride (PMSF). The homogenates were centrifuged at 100,000 g for 60 minutes at 4° C. The supernatant was filtered through 0.2 µM filter and loaded on a Pharmacia Mono Q anion exchange column (1 ml bed volume) that was equilibrated with 20 mM HEPES, 1 mM EDTA and 0.5 mM PMSF. After washing out unbound proteins, the enzymes were eluted with a linear gradient of 100–600 mM NaCl in the same buffer (35 to 50 ml total, depending on the tissue. Enzymes from the skeletal muscle, corpus cavernosum, retina, heart and platelet were eluted with 35, 40, 45, 50, and 50 ml respectively.) The column was run at a flow rate of 1 ml/min and 1 ml fractions were collected. The fractions comprising various PDE activities were pooled separately and used in later studies.

Measurement of Inhibition of PDEV

The PDE assay was carried out as described by Thompson and Appleman in *Biochemistry* 1971 10, 311–316 with minor modifications, as noted below.

The assays were adapted to a 96-well format. The enzyme was assayed in 5 mM MgCl$_2$, 15 mM Tris HCl (pH 7.4), 0.5 mg/ml bovine serum albumin, 1 µM cGMP or cAMP, 0.1 µCi [$^3$H]-cGMP or [$^3$H]-cAMP, and 2–10 µl of column elution. The total volume of the assay was 100 µl. The reaction mixture was incubated at 30° C. for 30 minutes. The reaction was stopped by boiling for 1 minute and then cooled down on ice. The resulting [$^3$H]5'-mononucleotides were further converted to uncharged [$^3$H]-nucleosides by adding 25 µl 1 mg/ml snake venom (*Ophiophagus hannah*) and incubating at 30° C. for 10 minute. The reaction was stopped by the addition of 1 ml Bio-Rad AG1-X2 resin slurry (1:3). All the charged nucleotides were bound by the resin and only uncharged [$^3$H]-nucleosides remained in the supernatant after centrifuging. An aliquot of 200 µl was taken and counted by liquid scintillation. PDE activity was expressed as pmol cyclic nucleotide hydrolyzed/min/ml of enzyme preparation.

Inhibitor studies were carried out in assay buffer with a final concentration of 10% DMSO. Under these conditions, the hydrolysis of product increased with time and enzyme concentration in a linear fashion.

Representative compounds of the present invention were tested according to the procedure described above, with results as listed in Table 1.

TABLE 1

| Compd # | IC$_{50}$ (nM) |
|---|---|
| 1 | 545.4 |
| 2 | 299.0 |

EXAMPLE 6

In Vitro Determination of K$_i$ for Phosphodiesterase Inhibitors

The assays are adapted to a 96-well format. Phosphodiesterase is assayed in 5 mM MgCl$_2$, 15 mM Tris HCl (pH 7.4), 0.5 mg/ml bovine serum albumin, 30 nM $^3$H-cGMP and test compound at various concentrations. The amount of enzyme used for each reaction is such that less than 15% of the initial substrate was converted during the assay period. For all measurements, the test compound is dissolved and diluted in 100% DMSO (2% DMSO in assay). The total volume of the assay is 100 µl. The reaction mixture is incubated at 30° C. for 90 minutes. The reaction is stopped by boiling for 1 minute and then immediately cooled by transfer to an ice bath. To each well is then added 25 µl 1 mg/ml snake venom (*Ophiophagus hannah*) and the reaction mixture incubating at 30° C. for 10 minute. The reaction is stopped by the addition of 1 ml Bio-Rad AG1-X2 resin slurry (1:3). An aliquot of 200 µl is taken and counted by liquid scintillation.

The % inhibition of the maximum substrate conversion (by the enzyme in the absence of inhibitor) is calculated for each test compound concentration. Using GraphPad Prism's nonlinear regression analysis (sigmoidal dose response), the % inhibition vs log of the test compound concentration is plotted to determine the IC$_{50}$. Under conditions where substrate concentration <<K$_m$ of the enzyme (K$_m$=substrate concentration at which half of the maximal velocity of the enzyme is achieved), K$_i$ is equivalent to the IC$_{50}$ value.

EXAMPLE 7

In vivo Testing

Following the procedure disclosed by Carter et al., (Carter, A. J., Ballard, S. A., and Naylor, A. M.) in The Journal of Urology 1998, 160, 242–246, the compounds of the present invention are tested for in vivo efficacy.

EXAMPLE 8

As a specific embodiment of an oral composition, 100 mg of the compound of Example 2 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of the formula (I):

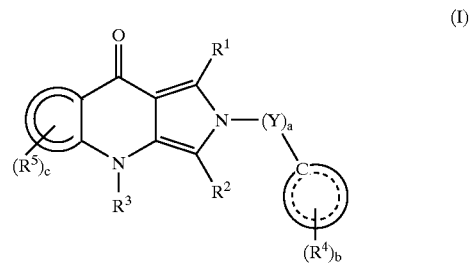

wherein

R$^1$ is selected from the group consisting of hydrogen, carboxy, —C(O)—C$_1$-C$_6$alkyl, —C(O)—C$_1$-C$_6$alkoxy, —C(O)NH—C$_1$-C$_6$alkyl-NH$_2$, —C(O)—NH—C$_1$-C$_6$alkyl-NHR$^A$, —C(O)—NH—C$_1$-C$_6$alkyl-N(R$^A$)$_2$, —C(O)—NH$_2$, —C(O)—NHR$^A$, —C(O)—N(R$^A$)$_2$, —C$_1$-C$_6$alkyl-NH$_2$, —C$_1$-C$_6$alkyl-NHR$^A$, —C$_1$-C$_6$alkyl-N(R$^A$)$_2$, —NH—C$_1$-C$_6$alkyl-N(R$^A$)$_2$;

where each $R^A$ is independently selected from the group consisting of $C_1$–$C_6$alkyl, aryl, $C_1$–$C_6$aralkyl and heteroaryl, where the aryl, aralkyl or heteroaryl may be optionally substituted with one to three $R^B$;

where each $R^B$ is independently selected from the group consisting of halogen, nitro, cyano, $C_1$–$C_6$alkyl, $C_1$–$C_6$alkoxy, $C_1$–$C_6$alkylcarbonyl, carboxy$C_1$–$C_6$alkyl, $C_1$–$C_6$alkylsulfonyl, trifluoromethyl, amino, di($C_1$–$C_6$alkyl)amino, acetylamino, carboxy$C_1$–$C_6$alkylcarbonylamino, hydroxy$C_1$–$C_6$alkylamino, NHR$^A$ and N(R$^A$)$_2$;

$R^2$ is selected from the group consisting of $C_5$–$C_{10}$alkyl (optionally substituted with one to three substituents independently selected from halogen, hydroxy, nitro, amino, NHR$^A$ or N(R$^A$)$_2$), aryl (optionally substituted with one to three substituents independently selected from R$^C$), cycloalkyl (optionally substituted with one to three substituents independently selected from R$^A$), heteroaryl (optionally substituted with one to three substituents independently selected from R$^C$), and heterocycloalkyl (optionally substituted with one to three substituents independently selected from R$^C$);

where $R^C$ is selected from the group consisting of halogen, nitro, cyano, $C_1$–$C_6$alkyl, $C_1$–$C_6$alkoxy, trifluoromethyl, trifluoromethoxy, NH$_2$, NH($C_1$–$C_6$alkyl) and N($C_1$–$C_6$alkyl)$_2$;

$R^3$ is selected from the group consisting of hydrogen, $C_1$–$C_6$alkyl, $C_1$–$C_6$alkylcarbonyl, $C_2$–$C_6$alkenylcarbonyl and $C_2$–$C_6$alkynylcarbonyl;

b is an integer from 0 to 4;

$R^4$ is independently selected from the group consisting of halogen, hydroxy, carboxy, oxo, nitro, $C_1$–$C_6$alkyl, $C_1$–$C_6$alkoxy, $C_1$–$C_6$alkoxycarbonyl, trifluoromethyl, phenyl (wherein the phenyl group may be optionally substituted with one to three substituents independently selected from R$^D$), phenylsulfonyl, naphthyl, $C_1$–$C_6$aralkyl, —O-aralkyl, (wherein the aralkyl group may be optionally substituted with one to three substituents independently selected from R$^D$), heteroaryl (wherein the heteroaryl may be optionally substituted with one to three substituents independently selected from R$^D$), heterocycloalkyl, NH$_2$, NHR$^A$, N(R$^A$)$_2$,

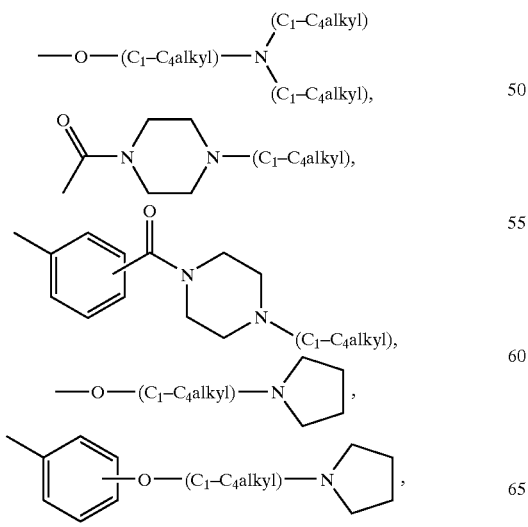

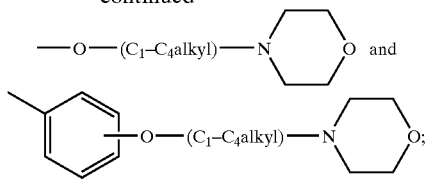

where each $R^D$ is independently selected from the group consisting of halogen, hydroxy, carboxy, oxo, $C_1$–$C_4$alkyl, $C_1$alkylthio, hydroxy$C_{1-4}$alkyl, $C_1$–$C_4$alkoxy, $C_1$–$C_4$alkyoxycarbonyl, $C_1$–$C_4$alkylcarbonyl, trifluoromethyl, trifluoromethoxy, NH$_2$, NHR$^A$, N(R$^A$)$_2$, C(O)N(R$^A$)$_2$, acetylamino, nitro, cyano, formyl, $C_1$–$C_6$alkylsulfonyl, carboxy$C_1$–$C_6$alkyl and aralkyl;

c is an integer from 0 to 4;

$R^5$ is independently selected from the group consisting of halogen, nitro, hydroxy, $C_1$–$C_6$alkyl, $C_1$–$C_6$alkoxy, —NH$_2$, —NHR$^A$, —N(R$^A$)$_2$, —OR$^A$, —C(O)NH$_2$, —C(O)NHR$^A$, —C(O)N(R$^A$)$_2$, —NHC(O)R$^A$, —SO$_2$NHR$^A$, —SO$_2$N(R$^A$)$_2$, where R$^A$ is as defined above, phenyl (optionally substituted with one to three substituents independently selected from R$^B$), heteroaryl (optionally substituted with one to three substituents independently selected from R$^B$) and heterocycloalkyl (optionally substituted with one to three substituents independently selected from R$^B$);

a is an integer from 0 to 1;

Y selected from the group consisting of —$C_1$–$C_6$alkyl-, —C(O)—, —($C_1$–$C_6$alkyl)carbonyl-, —($C_2$–$C_6$alkenyl)carbonyl-, —($C_2$–$C_6$alkynyl)carbonyl-, -carbonyl($C_1$–$C_6$alkyl)-, -carbonyl($C_2$–$C_6$alkenyl)-, —C(O)O—($C_1$–$C_6$alkyl)-, —C(S)—, —SO$_2$—, —($C_1$–$C_6$alkyl)sulfonyl-, -sulfonyl($C_1$–$C_6$alkyl)-, —C(O)NH—, —C(O)NH—($C_1$–$C_6$alkyl)-, —C(O)($C_3$–$C_7$cycloalkyl)- and —($C_3$–$C_7$cycloalkyl)—C(O)—;

is selected from the group consisting phenyl, furyl, thienyl and pyrrolyl;

is selected from the group consisting of aryl, heteroaryl, cycloalkyl and heterocycloalkyl;

provided that when $R^1$ is hydrogen, $R^3$ is hydrogen, b is 0, c is 0, a is 1, Y is —CH$_2$—,

is phenyl and

is phenyl, then $R^2$ is not trimethoxyphenyl;
or a pharmaceutically acceptable salt thereof.

2. The compound of claim 1 wherein
$R^1$ is hydrogen;
$R^2$ is selected from the group consisting of phenyl (optionally substituted with one to two substituent selected from halogen, nitro, cyano, $C_1$–$C_3$alkyl, $C_1$–$C_3$alkoxy, trifluoromethyl, trifluoromethoxy, $NH_2$, $NH(C_1$–$C_3$alkyl) or $N(C_1$–$C_3$alkyl)$_2$), heteroaryl and heterocycloalkyl;
$R^3$ is selected from the group consisting of H and $C_1$–$C_4$alkyl;
b is an integer from 0 to 4;
$R^4$ is selected from the group consisting of halogen, hydroxy, carboxy, oxo, $C_1$–$C_3$alkyl, $C_1$–$C_3$alkoxy, $C_1$–$C_3$alkoxycarbonyl, phenyl (wherein the phenyl may be optionally substituted with one to two substituents selected from hydroxy, carboxy, $C_1$–$C_4$alkyl, $C_{1-4}$alkylthio, hydroxy$C_{1-4}$alkyl, $C_1$–$C_4$alkoxy, $C_1$–$C_4$alkyoxycarbonyl, $C(O)N(R^4)_2$, trifluoromethyl, trifluoromethoxy, amino, ($C_{1-4}$alkyl)amino, di($C_{1-4}$alkyl)amino, nitro, cyano or formyl), O-aralkyl, heteroaryl (wherein the heteroaryl may be optionally substituted with one to two substituents selected from hydroxy, carboxy, oxo, $C_1$–$C_3$alkyl, $C_1$–$C_3$alkoxy, $C_1$–$C_3$alkyoxycarbonyl, $C(O)N(R^4)_2$, trifluoromethyl, trifluoromethoxy, amino, nitro, $C_1$–$C_3$alkylcarbonyl or $C_{1-4}$aralkyl), heterocycloalkyl,

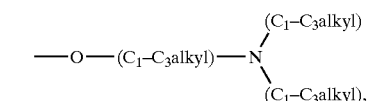

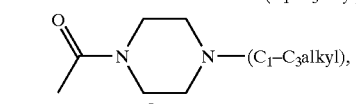

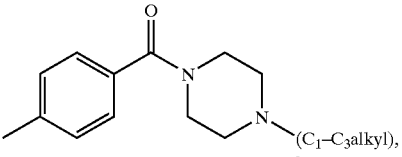

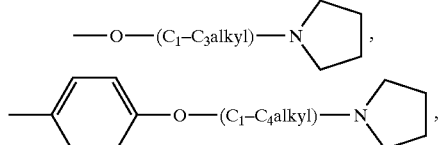

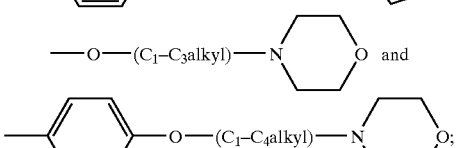

c is 0;
a is an integer from 0 to 1;
Y is selected from the group consisting of —$C_1$–$C_4$alkyl-, —C(S)—, —C(O)—, —C(O)O—($C_1$–$C_4$alkyl)-, —C(O)($C_1$–$C_4$alkyl)-, —C(O($C_2$–$C_4$alkenyl)-, C(O)—($C_3$–$C_7$cycloalkyl)- and —C(O)NH—($C_1$–$C_3$alkyl)-;

is phenyl;

is selected from the group consisting of phenyl, heteroaryl and heterocycloalkyl;
or a pharmaceutically acceptable salt thereof.

3. The compound of claim 2 wherein
$R_2$ is selected from the group consisting of 3,4-methylenedioxyphenyl, 3,4-dimethoxyphenyl, 5-(2,3-dihydrobenzofuryl), 3,4-dihydrobenzo-[1,4]-dioxin-6-yl, 5-benzofuryl, 5-indanyl and 3-thienyl;

$R^3$ is selected from the group consisting of H and methyl;

$R^4$ is selected from the group consisting of bromo, hydroxy, carboxy, oxo, methyl, phenyl, 4-hydroxyphenyl, 3-hydroxymethylphenyl, 4-hydroxymethylphenyl, 4-carboxyphenyl, 4-methylphenyl, 4-methoxyphenyl, 3,4-dimethoxyphenyl, 4-methoxycarbonyl, 4-methoxycarbonylphenyl, 3-trifluoromethylphenyl, 4-cyanophenyl, 4-aminophenyl, 4-dimethylaminophenyl, 3-nitrophenyl, 4-nitrophenyl, 4-formylphenyl, 4-methylthiophenyl, benzyloxy, 2-pyridinyl, 3-pyridinyl, 4-pyridinyl, N-oxy-2-pyridinyl, 3-thienyl, 2-furyl, 1-imidazolyl, 5-(1-benzyl-2-methylimidazolyl), 5-(1,2-dimethylimidazolyl), 5-(1-methylimidazoly), 5-(1-benzylimidazolyl), 3,4-methylenedioxyphenyl,

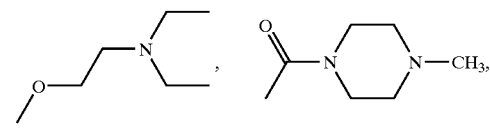

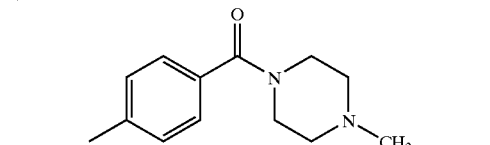

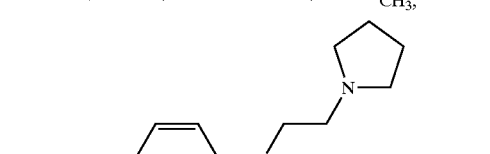

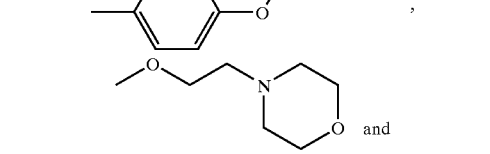

and

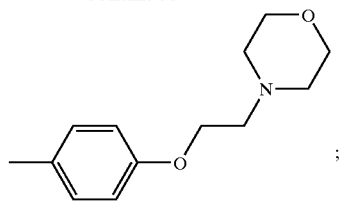

Y is selected from the group consisting of —CH₂—, —C(S)—, —C(O)—, —C(O)O—CH₂—, —C(O)—CH₂CH₂—, —C(O)CH=CH—, —C(O)NH—CH₂— (107), —C(O)-cyclopropyl and —C(O)CH₂;

is selected from the group consisting of phenyl, 2-furyl, 2-benzo(b)furyl, 2-pyrimidinyl, 2-pyridinyl, 3-pyridinyl, 4-pyridinyl, 1-imidazolyl, 2-imidazolyl, 2-thiazolyl, and 2-oxa-bicyclo[2.2.1]heptanyl;

or a pharmaceutically acceptable salt thereof.

4. The compound of claim 3 wherein

R² is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl;

R³ is H;

b is in integer from 0 to 1;

R⁴ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, 2-furyl, 3-thienyl, N-oxo-2-pyridinyl, 1-imidazolyl, 5-(1-benzyl-2-methylimidazolyl), 5-1,2-dimethylimidazolyl), 3,4-methylenedioxyphenyl,

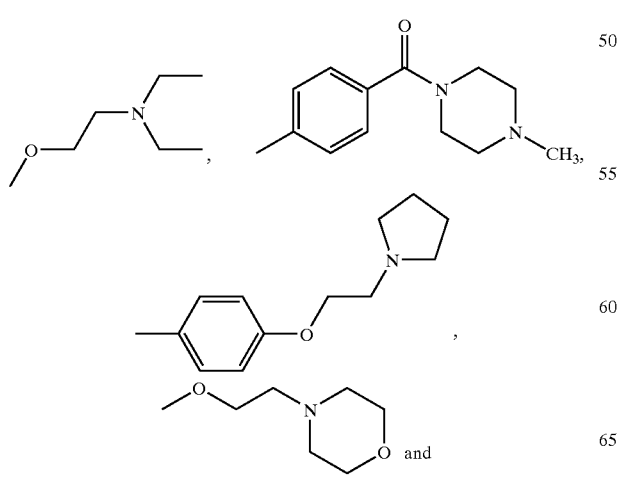

Y is selected from the group consisting of —C(O)—, —C(O)O—CH₂—, —C(O)—CH₂CH₂—, —C(O)—CH=CH—, and —C(O)-cyclopropyl;

is selected from the group consisting of phenyl, 2-furyl, 2-benzo(b)furyl, 2-pyrimidinyl, 2-pyridinyl, 3-pyridinyl, 4-pyridinyl and 2-thiazolyl;

or a pharmaceutically acceptable salt thereof.

5. The compound of claim 4 wherein

R² is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl;

R⁴ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, N-oxo-2-pyridinyl, 3-thienyl, 2-furyl, 1-imidazolyl, 5-(1-benzyl-2-methylimidazolyl), 5-(1,2dimethylimidazolyl), 3,4-methylenedioxyphenyl,

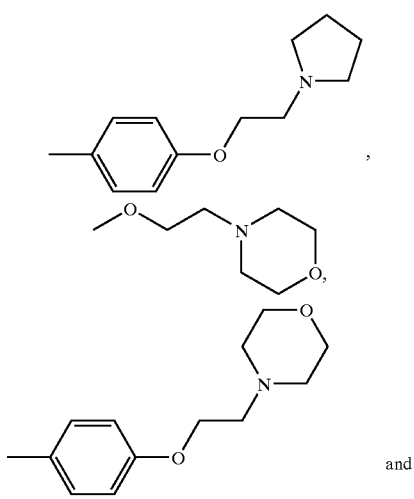

-continued

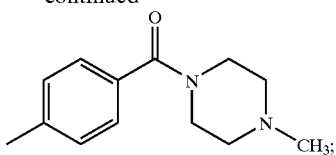

Y is selected from the group consisting of —C(O)—, —C(O)O—CH$_2$— and —C(O)—CH=CH—;

or a pharmaceutically acceptable salt thereof.

6. The compound of claim 5 wherein

R$^4$ is selected from the group consisting of 6-hydroxy, 4-carboxy, phenyl, 4-hydroxyphenyl, 3-hydroxymethylphenyl, 4-methylphenyl, 4-methylthiophenyl, 4-methoxyphenyl, 3,4-dimethoxyphenyl, 4-methoxycarbonyl, 3-trifluoromethylphenyl, 3-nitrophenyl, 4-nitrophenyl, 2-pyridinyl, 3-pyridinyl, 4-pyridinyl, N-oxo-2-pyridinyl, 3-thienyl, 5-(1-benzyl-2-methylimidazolyl), 5-(1,2-dimethylimidazolyl),

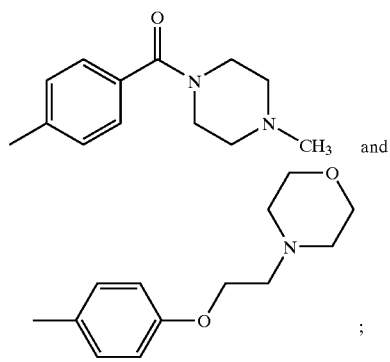

or a pharmaceutically acceptable salt thereof.

7. The compound of claim 6 wherein

R$^2$ is selected from the group consisting of 3,4-methylenedioxyphenyl, and 5-(2,3-dihydrobenzofuryl);

R$^4$ is selected from the group consisting of hydroxy, 4-methylphenyl, 4-methoxyphenyl, 3,4-dimethoxyphenyl, 4-methoxycarbonyl, 3-trifluoromethylphenyl, 4-nitrophenyl, 2-pyridinyl, 3-pyridinyl,

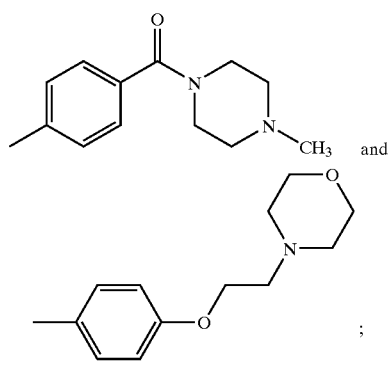

Y is selected from the group consisting of —C(O)— and —C(O)O—CH$_2$—;

is selected from the group consisting of 2-furyl, 2-benzo(b)furyl, 4-pyridinyl, 2-pyrimidinyl and 2-thiazolyl;

or a pharmaceutically acceptable salt thereof.

8. A compound of the formula (IV)

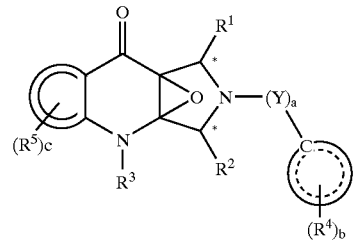

(IV)

wherein

R$^1$ is selected from the group consisting of hydrogen, carboxy, —C(O)—C$_1$-C$_6$alkyl, —C(O)—C$_1$-C$_6$alkoxy, —C(O)—NH—C$_1$-C$_6$alkyl-NH2, —C(O)—NH—C$_1$-C$_6$alkyl-NHR$^A$, —C(O)—NH—C$_1$-C$_6$alkyl-N(R$^A$)$_2$, —C(O)—NH$_2$, —C(O)—NHR$^A$, —C(O)—N(R$^A$)$_2$, —C$_1$-C$_6$alkyl-NH$_2$, —C$_1$-C$_6$alkyl-NHR$^A$, —C$_1$-C$_6$alkyl-N(R$^A$)$_2$, —NH—C$_1$-C$_6$alkyl-N(R$^A$)$_2$;

where each R$^A$ is independently selected from the group consisting of C$_1$-C$_6$alkyl, aryl, C$_1$-C$_6$aralkyl and heteroaryl, where the aryl, aralkyl or heteroaryl may be optionally substituted with one to three R$^B$;

where each R$^B$ is independently selected from the group consisting of halogen, nitro, cyano, C$_1$-C$_6$alkyl, C$_1$-C$_6$alkoxy, C$_1$-C$_6$alkylcarbonyl, carboxyC$_1$-C$_6$alkyl, C$_1$-C$_6$alkylsulfonyl, trifluoromethyl, amino, di(C$_1$-C$_6$alkyl)amino, acetylamino, carboxyC$_1$-C$_6$alkylcarbonylamino, hydroxyC$_1$-C$_6$alkylamino, NHR$^A$ and N(R$^A$)$_2$;

R$^2$ is selected from the group consisting of C$_5$-C$_{10}$alkyl (optionally substituted with one to three substituents independently selected from halogen, hydroxy, nitro, amino, NHR$^A$ or N(R$^A$)$_2$), aryl (optionally substituted with one to three substituents independently selected from R$^C$), cycloalkyl (optionally substituted with one to three substituents independently selected from R$^A$), heteroaryl (optionally substituted with one to three substituents independently selected from R$^C$), and heterocycloalkyl (optionally substituted with one to three substituents independently selected from R$^C$);

where R$^C$ is selected from the group consisting of halogen, nitro, cyano, C$_1$-C$_6$alkyl, C$_1$-C$_6$alkoxy, trifluoromethyl, trifluoromethoxy, NH$_2$, NH(C$_1$-C$_6$alkyl) and N(C$_1$-C$_6$alkyl)$_2$;

R$^3$ is selected from the group consisting of hydrogen, C$_1$-C$_6$alkyl, C$_1$-C$_6$alkylcarbonyl, C$_2$-C$_6$alkenylcarbonyl and C$_2$-C$_6$alkynylcarbonyl;

b is an integer from 0 to 4;

R$^4$ is independently selected from the group consisting of halogen, hydroxy, carboxy, oxo, nitro, C$_1$-C$_6$alkyl, C$_1$-C$_6$alkoxy, C$_1$-C$_6$alkoxycarbonyl, trifluoromethyl, phenyl (wherein the phenyl group may be optionally substituted with one to three substituents independently selected from R$^D$), phenylsulfonyl, naphthyl, C$_1$–C$_6$aralkyl, —O-aralkyl, (wherein the aralkyl group may be optionally substituted with one to three substituents independently selected from R$^D$), heteroaryl (wherein the heteroaryl may be optionally substituted with one to three substituents independently selected from R$^D$), heterocycloalkyl, NH$_2$,

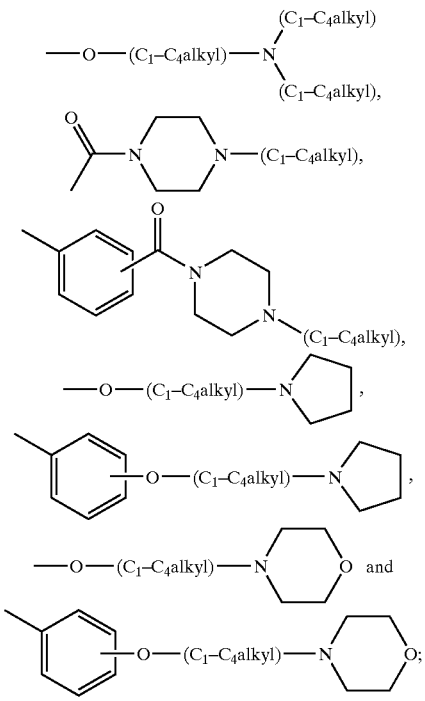

where each R$^D$ is independently selected from the group consisting of halogen, hydroxy, carboxy, oxo, C$_1$–C$_4$alkyl, C$_{1-4}$alkylthio, hydroxyC$_{1-4}$alkyl, C$_1$–C$_4$alkoxy, C$_1$–C$_4$alkyoxycarbonyl, C$_1$–C$_4$alkylcarbonyl, trifluoromethyl, trifluoromethoxy, NH$_2$, NHR$^A$, N(R$^A$)$_2$, C(O)N(R$^A$)$_2$, acetylamino, nitro, cyano, formyl, C$_1$–C$_6$alkylsulfonyl, carboxyC$_1$–C$_6$alkyl and aralkyl;

c is an integer from 0 to 4;

R$^5$ is independently selected from the group consisting of halogen, nitro, hydroxy, C$_1$–C$_6$alkyl, C$_1$–C$_6$alkoxy, —NH$_2$, —NHR$^A$, —N(R$^A$)$_2$, —OR$^A$, —C(O)NH$_2$, —C(O)NHR$^A$, —C(O)N(R$^A$)$_2$, —NHC(O)R$^A$, —SO$_2$NHR$^A$, —SO$_2$N(R$^A$)$_2$, where R$^A$ is as defined above, phenyl (optionally substituted with one to three substituents independently selected from R$^B$), heteroaryl (optionally substituted with one to three substituents independently selected from R$^B$) and heterocycloalkyl (optionally substituted with one to three substituents independently selected from R$^B$);

a is an integer from 0 to 1;

Y selected from the group consisting of —C$_1$–C$_6$alkyl-, —C(O)—, —(C$_1$–C$_6$alkyl)carbonyl-, —(C$_2$–C$_6$alkenyl)carbonyl-, —(C$_2$–C$_6$alkynyl)carbonyl-, -carbonyl(C$_1$–C$_6$alkyl)-, -carbonyl(C$_2$–C$_6$alkenyl)-, —C(O)O—(C$_1$–C$_6$alkyl)-, —C(S)—, —SO$_2$—, —(C$_1$–C$_6$alkyl)sulfonyl-, -sulfonyl(C$_1$–C$_6$alkyl)-, —C(O)NH—, —C(O)NH—(C$_1$–C$_6$alkyl)-, —C(O)(C$_3$–C$_7$cycloalkyl) and —(C$_3$–C$_7$cycloalkyl)-C(O)—;

is selected from the group consisting phenyl, furyl, thienyl and pyrrolyl;

is selected from the group consisting of aryl, heteroaryl, cycloalkyl and heterocycloalkyl;

or a pharmaceutically acceptable salt thereof.

9. The compound of claim 8 wherein

R$^1$ is hydrogen;

R$^2$ is selected from the group consisting of phenyl (optionally substituted with one to two substituent selected from,halogen, nitro, cyano, C$_1$–C$_3$alkyl, C$_1$–C$_3$alkoxy, trifluoromethyl, trifluoromethoxy, NH$_2$, NH(C$_1$–C$_3$alkyl) or N(C$_1$–C$_3$alkyl)), heteroaryl and heterocycloalkyl;

R$^3$ is selected from the group consisting of H and C$_1$–C$_4$alkyl;

b is an integer from 0 to 4;

R$^4$ is selected from the group consisting of halogen, hydroxy, carboxy, oxo, C$_1$–C$_3$alkyl, C$_1$–C$_3$alkoxy, C$_1$–C$_3$alkoxycarbonyl, phenyl (wherein the phenyl may be optionally substituted with one to two substituents selected from hydroxy, carboxy, C$_1$–C$_4$alkyl, C$_{1-4}$alkylthio, hydroxyC$_{1-4}$alkyl, C$_1$–C$_4$alkoxy, C$_1$–C$_4$alkyoxycarbonyl, C(O)N(R$^A$)$_2$, trifluoromethyl, trifluoromethoxy, amino, (C$_{1-4}$alkyl)amino, di(C$_{1-4}$alkyl)amino, nitro, cyano or formyl), O-aralkyl, heteroaryl (wherein the heteroaryl may be optionally substituted with one to two substituents selected from hydroxy, carboxy, oxo, C$_1$–C$_3$alkyl, C$_1$–C$_3$alkoxy, C$_1$–C$_3$alkyoxycarbonyl, C(O)N(R$^A$)$_2$, trifluoromethyl, trifluoromethoxy, amino, nitro, C$_1$–C$_3$alkylcarbonyl or C$_{1-4}$aralkyl), heterocycloalkyl,

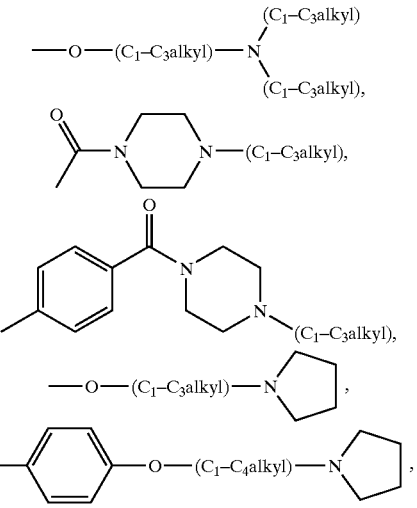

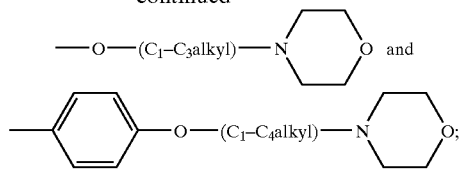

c is 0;

a is an integer from 0 to 1;

Y is selected from the group consisting of —$C_1$–$C_4$alkyl-, —C(S)—, —C(O)—, —C(O)O—($C_1$–$C_4$alkyl)-, —C(O)—($C_1$–$C_4$alkyl)-, —C(O)—($C_2$–$C_4$alkenyl)-, C(O)—($C_3$–$C_7$cycloalkyl)- and —C(O)NH—($C_1$–$C_3$alkyl)-;

is phenyl;

is selected from the group consisting of phenyl, heteroaryl and heterocycloalkyl;

or a pharmaceutically acceptable salt thereof.

10. The compound of claim 9 wherein $R^2$ is selected from the group consisting of 3,4-methylenedioxyphenyl, 3,4-dimethoxyphenyl, 5-(2,3-dihydrobenzofuryl), 3,4-dihydrobenzo-[1,4]-dioxin-6-yl, 5-benzofuryl, 5-indanyl and 3-thienyl;

$R^3$ is selected from the group consisting of H and methyl;

$R^4$ is selected from the group consisting of bromo, hydroxy, carboxy, oxo, methyl, phenyl, 4-hydroxyphenyl, 3-hydroxymethylphenyl, 4-hydroxymethylphenyl, 4-carboxyphenyl, 4-methylphenyl, 4-methoxyphenyl, 3,4-dimethoxyphenyl, 4-methoxycarbonyl, 4-methoxycarbonylphenyl, 3-trifluoromethylphenyl, 4-cyanophenyl, 4-aminophenyl, 4-dimethylaminophenyl, 3-nitrophenyl, 4-nitrophenyl, 4-formylphenyl, 4-methylthiophenyl, benzyloxy, 2-pyridinyl, 3-pyridinyl, 4-pyridinyl, N-oxy-2-pyridinyl, 3-thienyl, 2-furyl, 1-imidazolyl, 5-(1-benzyl-2-methylimidazolyl), 5-(1,2-dimethylimidazolyl), 5-(1-methylimidazolyl), 5-(1-benzylimidazolyl), 3,4-methylenedioxyphenyl,

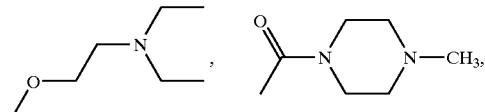

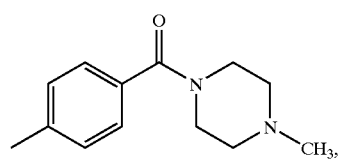

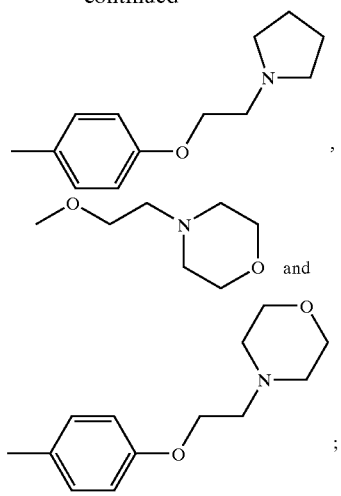

Y is selected from the group consisting of —$CH_2$—, —C(S)—, —C(O)—, —C(O)O—$CH_2$—, —C(O)—$CH_2CH_2$—, —C(O)—CH=CH—, —C(O)NH—$CH_2$— (107), —C(O)-cyclopropyl and —C(O)$CH_2$;

is selected from the group consisting of phenyl, 2-furyl, 2-benzo(b)furyl, 2-pyrimidinyl, 2-pyridinyl, 3-pyridinyl, 4-pyridinyl, 1-imidazolyl, 2-imidazolyl, 2-thiazolyl, and 2-oxa-bicyclo[2.2.1]heptanyl;

or a pharmaceutically acceptable salt thereof.

11. The compound of claim 10 wherein $R^2$ is selected from the group consisting of 3,4-methylenedioxyphenyl, 5-(2,3-dihydrobenzofuryl), 3,4-dihydrobenzo-[1,4]-dioxin-6-yl, 3-thienyl, 5-indanyl and 5-benzofuryl;

$R^3$ is H;

b is in integer from 0 to 1;

$R^4$ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, 2-furyl, 3-thienyl, N-oxo-2-pyridinyl, 1-imidazolyl, 5-(1-benzyl-2-methylimidazolyl), 5-(1,2-dimethylimidazolyl), 3,4-methylenedioxyphenyl,

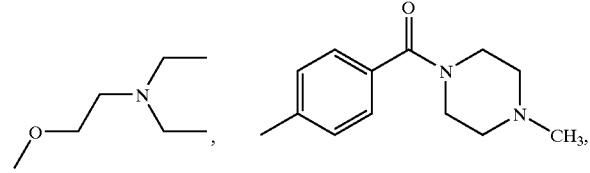

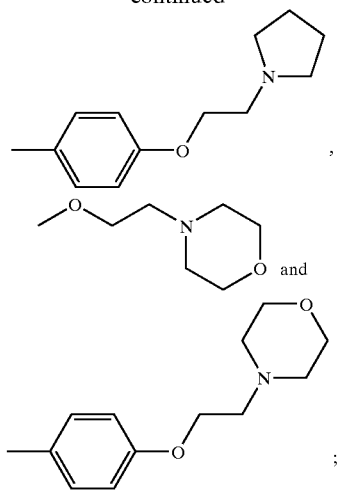

Y is selected from the group consisting of —C(O)—, —C(O)O—CH₂—, —C(O)—CH₂CH₂—, —C(O)—CH=CH—, and —C(O)-cyclopropyl;

is selected from the group consisting of phenyl, 2-furyl, 2-benzo(b)furyl, 2-pyrimidinyl, 2-pyridinyl, 3-pyridinyl, 4-pyridinyl and 2-thiazolyl;

or a pharmaceutically acceptable salt thereof.

12. The compound of claim 11 wherein

R² is selected from the group consisting of 3,4-methylenedioxyphenyl, 5-(2,3-dihydrobenzofuryl), 3,4-dihydrobenzo-[1,4]-dioxin-4-yl, 3-thienyl, 5-indanyl and 5-benzofuryl;

R⁴ is selected from the group consisting of 5-bromo, 2-hydroxy, 6-hydroxy, 4-carboxy, phenyl, 4-hydroxyphenyl, 3-hydroxymethylphenyl, 4-hydroxymethylphenyl, 4-carboxyphenyl, 4-methylphenyl, 4-methylthiophenyl, 4-methoxyphenyl, 3,4-dimethoxyphenyl, 4-methoxycarbonyl, 4-methoxycarbonylphenyl, 3-trifluoromethylphenyl, 4-aminophenyl, 4-dimethylaminophenyl, 3-nitrophenyl, 4-nitrophenyl, 4-cyanophenyl, 4-formylphenyl, benzyloxy, 2-pyridinyl, 3-pyridinyl, 4-pyridinyl, N-oxo-2-pyridinyl, 3-thienyl, 2-furyl, 1-imidazolyl, 5-(1-benzyl-2-methylimidazolyl), 5-(1,2-dimethylimidazolyl), 3,4-methylenedioxyphenyl,

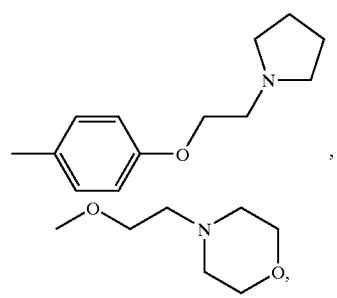

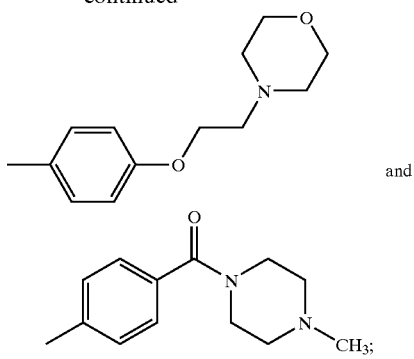

Y is selected from the group consisting of —C(O)—, —C(O)O—CH₂— and —C(O)—CH=CH—;

or a pharmaceutically acceptable salt thereof.

13. The compound of claim 12 wherein

R⁴ is selected from the group consisting of 6-hydroxy, 4-carboxy, phenyl, 4-hydroxyphenyl, 3-hydroxymethylphenyl, 4-methylphenyl, 4-methylthiophenyl, 4-methoxyphenyl, 3,4-dimethoxyphenyl, 4-methoxycarbonyl, 3-trifluoromethylphenyl, 3-nitrophenyl, 4-nitrophenyl, 2-pyridinyl, 3-pyridinyl, 4-pyridinyl, N-oxo-2-pyridinyl, 3-thienyl, 5-(1-benzyl-2-methylimidazolyl), 5-(1,2-dimethylimidazolyl),

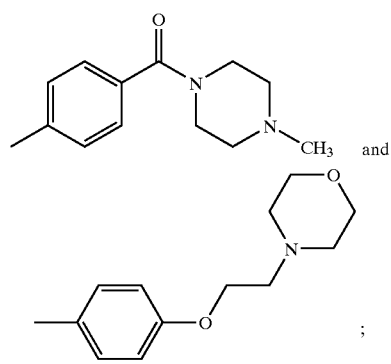

or a pharmaceutically acceptable salt thereof.

14. The compound of claim 13 wherein

R² is selected from the group consisting of 3,4-methylenedioxyphenyl, and 5-(2,3-dihydrobenzofuryl);

R⁴ is selected from the group consisting of hydroxy, 4-methylphenyl, 4-methoxyphenyl, 3,4-dimethoxyphenyl, 4-methoxycarbonyl, 3-trifluoromethylphenyl, 4-nitrophenyl, 2-pyridinyl, 3-pyridinyl,

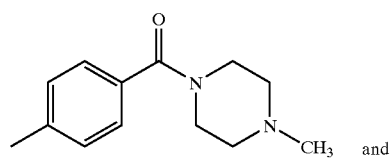

-continued

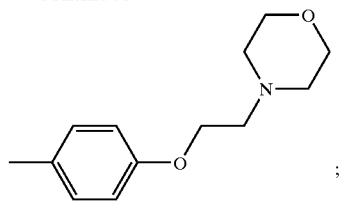

Y is selected from the group consisting of —C(O)— and —C(O)O—CH$_2$—;

is selected from the, group consisting of 2-furyl, 2-benzo(b)furyl, 4-pyridinyl, 2-pyrimidinyl and 2-thiazolyl;

or a pharmaceutically acceptable salt thereof.

15. A pharmaceutical composition comprising a pharmaceutically acceptable carrier and a compound of claim 1.

16. A pharmaceutical composition made by mixing a compound of claim 1 and a pharmaceutically acceptable carrier.

17. A process for making a pharmaceutical composition comprising mixing a compound of claim 1 and a pharmaceutically acceptable carrier.

18. A method of treating sexual dysfunction in a subject in need thereof comprising administering to the subject a therapeutically effective amount of the compound of claim 1.

19. A method of treating sexual dysfunction in a subject in need thereof comprising administering to the subject a therapeutically effective amount of the composition of claim 15.

20. The method of treating sexual dysfunction of claim 18, wherein the sexual dysfunction is male sexual dysfunction, male erectile dysfunction, impotence, female sexual dysfunction, female sexual arousal dysfunction and female sexual dysfunction related to blood flow and nitric oxide production in the tissues of the vagina and clitoris.

21. A method for increasing the concentration of cGMP in penile tissue in a male subject in need thereof comprising administering to the subject an effective amount of the compound of claim 1.

22. A method of treating a condition selected from the group consisting of male erectile dysfunction (ED), impotence, female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of the compound of claim 1.

* * * * *